United States Patent
Fuimaono et al.

(10) Patent No.: US 6,628,976 B1
(45) Date of Patent: Sep. 30, 2003

(54) CATHETER HAVING MAPPING ASSEMBLY

(75) Inventors: Kristine B. Fuimaono, Covina, CA (US); Michel Haissaguerre, Talence (FR)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/551,467

(22) Filed: Apr. 17, 2000

Related U.S. Application Data

(60) Provisional application No. 60/178,478, filed on Jan. 27, 2000.

(51) Int. Cl.$^7$ ............................................. A61B 5/04
(52) U.S. Cl. .................. 600/374; 600/585; 604/532; 128/898
(58) Field of Search .................. 606/41, 49; 607/99, 607/113, 122; 604/532; 600/374, 585; 128/898

(56) References Cited

U.S. PATENT DOCUMENTS

| | | | |
|---|---|---|---|
| 4,777,955 A | 10/1988 | Brayton et al. | 128/642 |
| 4,882,777 A | 11/1989 | Narula | 604/281 |
| 4,920,980 A | 5/1990 | Jackowski | 128/786 |
| 4,960,134 A | 10/1990 | Webster, Jr. | 128/786 |
| 4,984,581 A | 1/1991 | Stice | 128/772 |
| 5,170,787 A | 12/1992 | Lindegren | 128/642 |
| 5,255,679 A | 10/1993 | Imran | 128/642 |
| 5,263,493 A | 11/1993 | Avitall | 607/122 |
| 5,275,162 A | 1/1994 | Edwards et al. | 128/642 |
| 5,327,905 A | 7/1994 | Avitall | 128/772 |
| 5,354,297 A | 10/1994 | Avitall | 606/45 |
| 5,383,923 A | 1/1995 | Webster, Jr. | 607/125 |
| 5,445,148 A | 8/1995 | Jaraczewski et al. | 128/642 |
| 5,487,385 A | 1/1996 | Avitall | 128/642 |
| 5,545,200 A | 8/1996 | West et al. | 607/122 |
| 5,549,581 A | 8/1996 | Lurie et al. | 604/282 |
| 5,582,609 A | 12/1996 | Swanson et al. | 606/39 |

(List continued on next page.)

FOREIGN PATENT DOCUMENTS

EP 0 499 491 A2 8/1992

OTHER PUBLICATIONS

M. Haissaguerre et al., "Spontaneous Initiation of Atrial Fibrillation by Ectopic Beats Originating in the Pulmonary Veins", The New England Journal of Medicine, 339:659–666 (Sep. 3), 1998.

*Primary Examiner*—Linda C. M. Dvorak
*Assistant Examiner*—David M. Ruddy
(74) *Attorney, Agent, or Firm*—Christie, Parker & Hale, LLP

(57) ABSTRACT

A mapping catheter comprises a catheter body and a mapping assembly. The catheter body has an outer wall, proximal and distal ends, and at least one lumen extending therethrough. The mapping assembly comprises a generally straight proximal region attached to the catheter body, a generally circular main region distal the proximal region having an outer circumference, and a generally straight distal region distal the main region. The mapping assembly also comprises a support member having shape-memory, a non-conductive covering over the support member, and a plurality of electrodes on the non-conductive covering along the generally circular main region.

82 Claims, 5 Drawing Sheets

U.S. PATENT DOCUMENTS

| | | | |
|---|---|---|---|
| 5,617,854 A | 4/1997 | Munsif | 128/642 |
| 5,626,136 A | 5/1997 | Webster, Jr. | 128/642 |
| 5,642,736 A | 7/1997 | Avitall | 128/772 |
| 5,673,695 A | 10/1997 | McGee et al. | 128/642 |
| 5,680,860 A | 10/1997 | Imran | 128/642 |
| 5,730,127 A | 3/1998 | Avitall | 128/642 |
| 5,755,760 A | 5/1998 | Maguire et al. | 607/122 |
| 5,797,905 A | 8/1998 | Fleischman et al. | 606/41 |
| 5,800,428 A | 9/1998 | Nelson et al. | 606/41 |
| 5,827,278 A | 10/1998 | Webster, Jr. | 606/41 |
| 5,836,947 A | 11/1998 | Fleischman et al. | 606/47 |
| 5,860,920 A | 1/1999 | McGee et al. | 600/374 |
| 5,865,800 A | 2/1999 | Mirarchi et al. | 604/95 |
| 5,879,295 A | 3/1999 | Li et al. | 600/373 |
| 5,882,333 A | 3/1999 | Schaer et al. | 604/95 |
| 5,882,346 A | 3/1999 | Pomeranz et al. | 604/280 |
| 5,931,811 A | 8/1999 | Haissaguerre et al. | 604/95 |
| 5,935,102 A | 8/1999 | Bowden et al. | 604/95 |
| 5,938,694 A | 8/1999 | Jaraczewski et al. | 607/122 |
| 5,951,471 A | 9/1999 | de la Rama et al. | 600/381 |
| 5,984,909 A | 11/1999 | Lurie et al. | 604/282 |
| 5,997,526 A | 12/1999 | Giba et al. | 604/531 |
| 6,002,955 A | 12/1999 | Willems et al. | 600/374 |
| 6,035,224 A | 3/2000 | West | 600/373 |
| 6,064,902 A | 5/2000 | Haissaguerre et al. | 600/381 |
| 6,088,614 A | 7/2000 | Swanson | 600/510 |
| 6,090,104 A | 7/2000 | Webster, Jr. | 606/41 |
| 6,096,036 A | 8/2000 | Bowe et al. | 606/41 |
| 6,106,522 A | 8/2000 | Fleischman et al. | 606/41 |
| 6,129,724 A | 10/2000 | Fleischman et al. | 606/41 |
| 6,146,381 A | 11/2000 | Bowe et al. | 606/41 |
| 6,169,916 B1 | 1/2001 | West | 600/373 |
| 6,325,797 B1 * | 12/2001 | Stewart et al. | 606/41 |

* cited by examiner

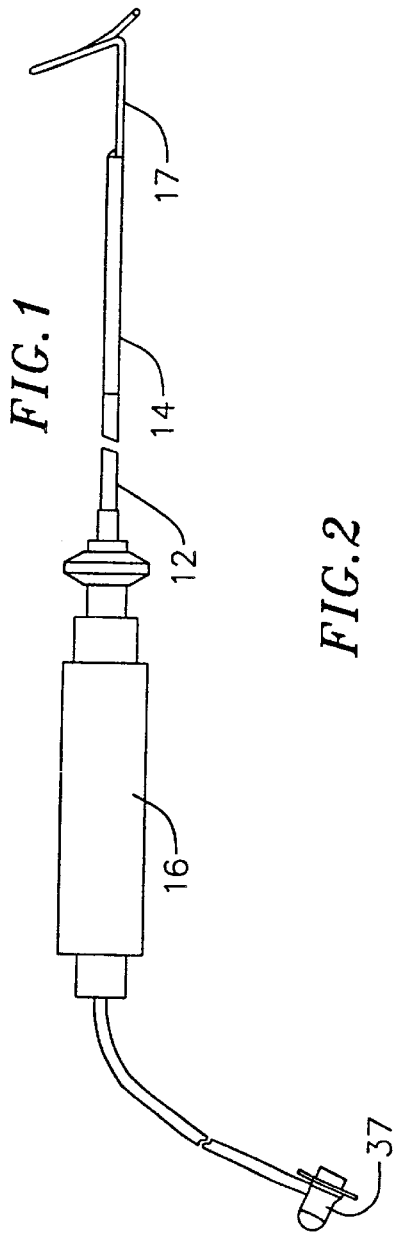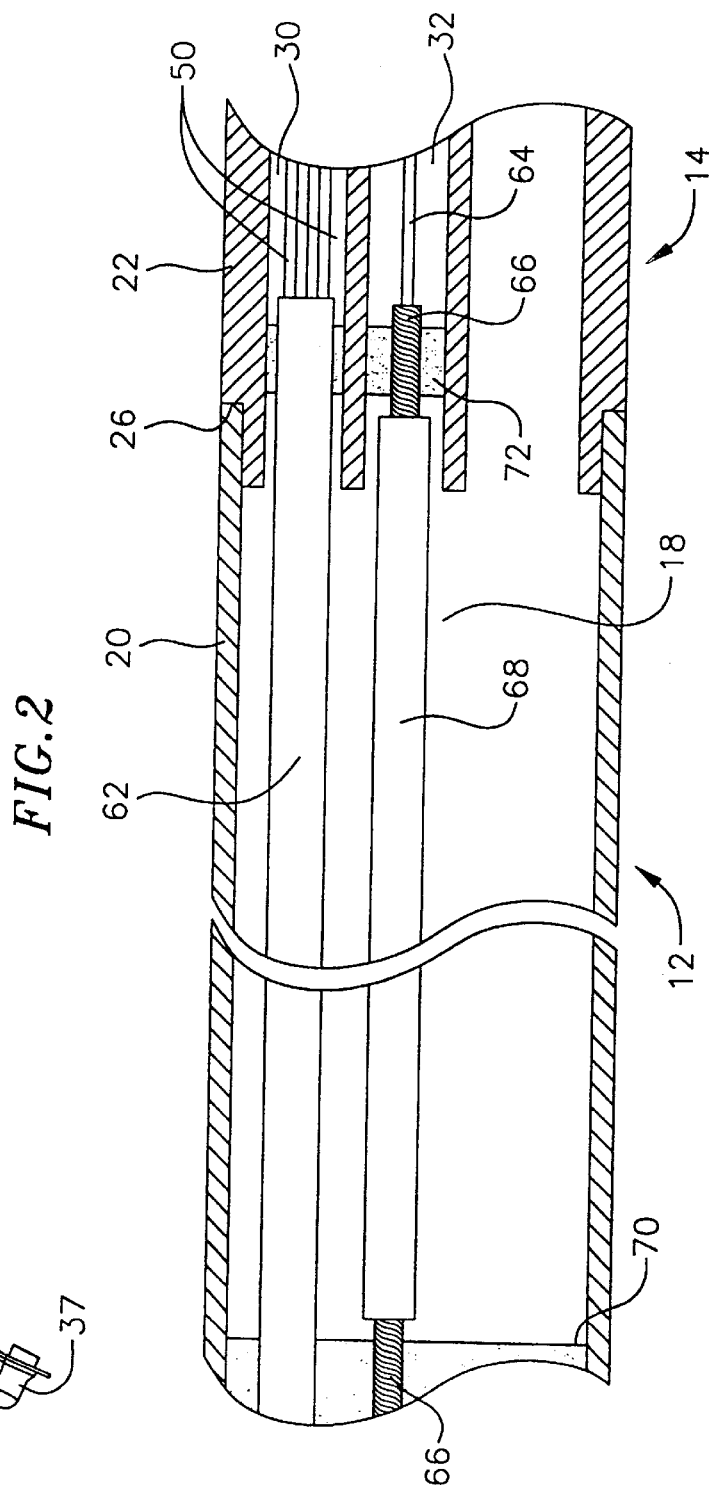

CATHETER HAVING MAPPING ASSEMBLY

This application claims priority pursuant to 35 USC §119(e) and 37 CFR §1.78(a)(4) to U.S. Provisional Application No. 60/178,478, filed Jan. 27, 2000.

FIELD OF THE INVENTION

The present invention relates to an improved mapping catheter that is particularly useful for mapping electrical activity in a tubular region of or near the heart.

BACKGROUND OF THE INVENTION

Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination. None of the proposed techniques, however, provide for measurement of the activity within a pulmonary vein, coronary sinus or other tubular structure about the inner circumference of the structure.

SUMMARY OF THE INVENTION

The present invention is directed to a catheter having a mapping assembly and a method for measuring electrical activity within a tubular region of or near the heart, e.g., a pulmonary vein, the coronary sinus, the superior vena cava, or the pulmonary outflow tract. The mapping assembly, which has a generally circular region with a series of spaced-apart electrodes mounted thereon, is positioned within the tubular region so that the electrodes are in contact with an inner generally circumferential surface inside the tubular structure.

In one embodiment, the invention is directed to a mapping catheter comprising an elongated tubular catheter body and a mapping assembly mounted at the distal end of the catheter body. The catheter body has an outer wall, proximal and distal ends, and at least one lumen extending therethrough. The mapping assembly comprises a tubular structure having a generally straight proximal region attached to the catheter body, a generally circular main region generally transverse and distal to the proximal region having an outer circumference, a transition region connecting the proximal region and the main region, and a generally straight distal region distal the main region, preferably extending substantially tangentially to the generally circular main region. The tubular structure comprises a non-conductive cover over at least the main region of the mapping assembly. The assembly further comprises a support member having shape-memory disposed within at least the main region of the mapping assembly. A plurality of spaced-apart electrodes are carried by the generally circular main region of the mapping assembly.

In another embodiment, the invention is directed to a method for mapping electrical activity within a tubular region of or near the heart, wherein the tubular region has an inner generally circumferential surface. The method comprises inserting the distal end of a catheter as described above into the heart. The outer circumference of the generally circular main region of the mapping assembly is contacted with the inner generally circumferential surface of the tubular region. The electrical activity within the tubular region is mapped with the electrodes of the generally circular main region. The method is particularly useful for mapping tubular regions such as pulmonary veins, the coronary sinus, the superior vena cava, and the pulmonary outflow tract.

DESCRIPTION OF THE DRAWINGS

These and other features and advantages of the present invention will be better understood by reference to the following detailed description when considered in conjunction with the accompanying drawings wherein:

FIG. 1 is a side cross-sectional view of an embodiment of the catheter of the invention.

FIG. 2 is a side cross-sectional view of a catheter body according to the invention, including the junction between the catheter body and intermediate section.

DETAILED DESCRIPTION

Figure 3:
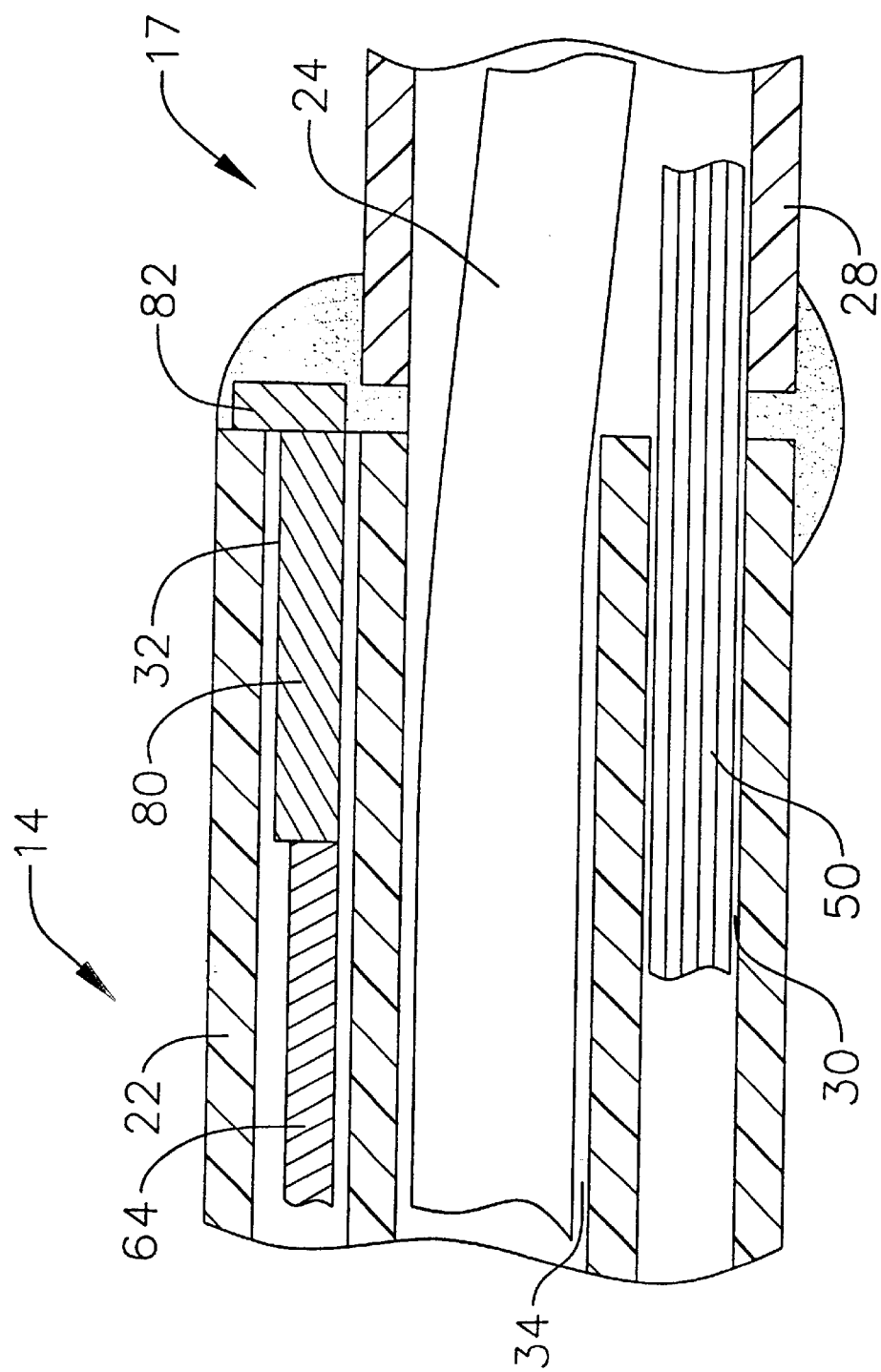
FIG. 3 is a cross-sectional view of the intermediate section, including the junction between the intermediate section and the mapping assembly.

In a particularly preferred embodiment of the invention, there is provided a catheter having a mapping assembly at its distal end. As shown in FIG. 1, the catheter comprises an elongated catheter body 12 having proximal and distal ends, a intermediate section 14 at the distal end of the catheter body, a control handle 16 at the proximal end of the catheter body, and a mapping assembly 17 mounted at the distal end of the catheter to the intermediate section.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like to increase torsional stiffness of the catheter body 12 so that, when the control handle 16 is rotated, the intermediate section 14 of the catheter 10 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate a puller wire, lead wires, and any other desired wires, cables or tubes. If desired, the inner surface of the outer wall 20 is lined with a stiffening tube (not shown) to provide improved torsional stability. A particularly preferred catheter has an outer wall 20 with an outer diameter of from about 0.090 inch to about 0.94 inch and an inner diameter of from about 0.061 inch to about 0.065 inch.

The intermediate section 14 comprises a short section of tubing 22 having three lumens. The first lumen 30 electrode carries lead wires 50, the second lumen 32 carries a puller wire 64, and the third lumen 34 carries a support member 24. The tubing 22 is made of a suitable non-toxic material that is preferably more flexible than the catheter body 12. A presently preferred material for the tubing 22 is braided polyurethane, i.e., polyurethane with an embedded mesh of braided stainless steel or the like. The size of each lumen is not critical, but is sufficient to house the lead wires, puller wire or support member.

The useful length of the catheter, i.e., that portion that can be inserted into the body excluding the mapping assembly 17, can vary as desired. Preferably the useful length ranges from about 110 cm to about 120 cm. The length of the intermediate section 14 is a relatively small portion of the useful length, and preferably ranges from about 3.5 cm to about 10 cm, more preferably 6 from about 5 cm to about 6.5 cm.

A preferred means for attaching the catheter body 12 to the intermediate section 14 is illustrated in FIG. 2. The proximal end of the intermediate section 14 comprises an outer circumferential notch 26 that receives the inner surface of the outer wall 22 of the catheter body 12. The intermediate section 14 and catheter body 12 are attached by glue or the like.

If desired, a spacer (not shown) can be located within the catheter body between the distal end of the stiffening tube (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

At the distal end of the intermediate section 14 is a mapping assembly, as shown in FIGS. 3 to 7. The mapping assembly is formed from the distal end of the support member 24 covered by a non-conductive covering 28. The mapping assembly comprises a generally straight proximal region 38, a generally circular main region 39 and a generally straight distal region 40. The proximal region 38 is mounted on the intermediate section 14, as described in more detail below, so that its axis is generally parallel to the axis of the intermediate section. The proximal region 38 preferably has an exposed length, e.g, not contained within the intermediate section 14, ranging from about 3 mm to about 12 mm, more preferably about 3 mm to about 8 mm, still more preferably about 5 mm inch, but can vary as desired.

Figure 4:
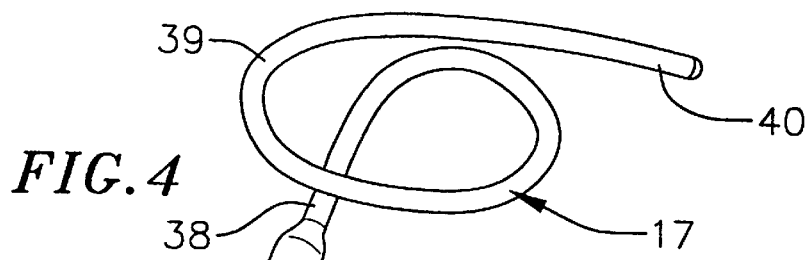
FIG. 4 is a schematic perspective view of the mapping assembly according to the invention.
Figure 5:
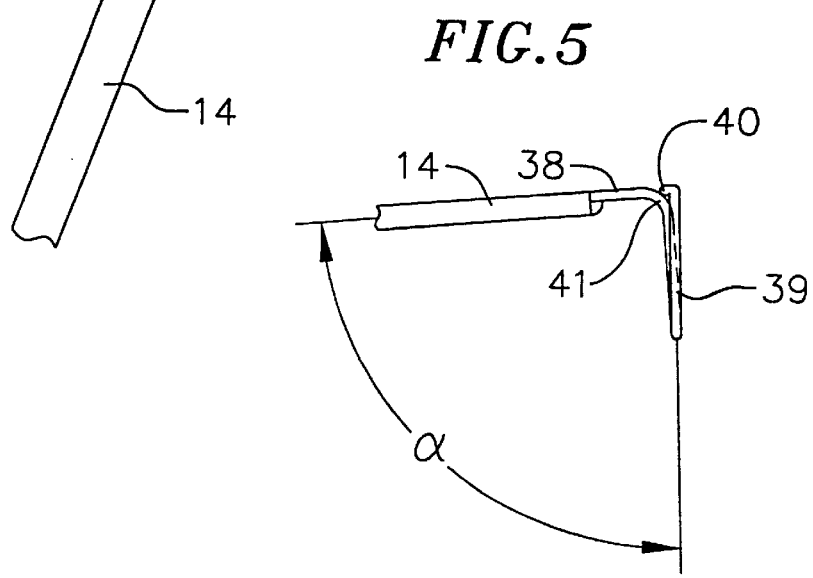
FIG. 5 is a side view of the mapping assembly according to the invention in a clockwise formation.
Figure 6:
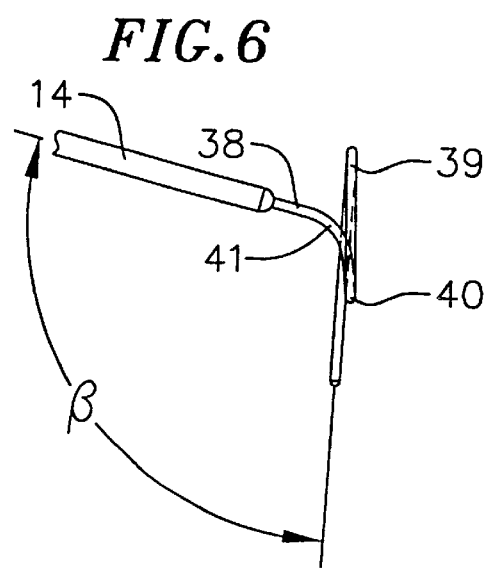
FIG. 6 is a side view of the mapping assembly according to the invention in a counterclockwise formation rotated 90° relative to the assembly depicted in FIG. 5.

The generally circular main region 39 does not form a flat circle, but is very slightly helical, as shown in FIGS. 4 to 6. The main region 39 has an outer diameter preferably ranging to about 10 mm to about 25 mm, more preferably about 12 mm to about 20 mm, still more preferably about 15 mm. The transition region 41 of the straight proximal region 38 and generally circular main region 39 is slightly curved and formed such that, when viewed from the side with the proximal region at the top of the circular main region as shown in FIG. 5, the proximal region (along with the intermediate section 14) forms an angle α with the curved region ranging from about 75° to about 95°, preferably from about 83° to about 93°, more preferably about 87°. The main region 39 can curve in a clockwise direction, as shown in FIG. 5, or a counterclockwise direction, as shown in FIG. 6. When the assembly 17 is turned 90°, as shown in FIG. 6, so that the transition region 41 is near the center of the main region, the proximal region (along with the intermediate section 14) forms an angle β with the main region ranging from about 90° to about 135°, preferably from about 100° to about 110°, more preferably about 105°.

The support member 24 is made of a material having shape-memory, i.e., that can be straightened or bent out of its original shape upon exertion of a force and is capable of substantially returning to its original shape upon removal of the force. A particularly preferred material for the support member 24 is a nickel/titanium alloy. Such alloys typically comprise about 55% nickel and 45% titanium, but may comprise from about 54% to about 57% nickel with the balance being titanium. A preferred nickel/titanium alloy is nitinol, which has excellent shape memory, together with ductility, strength, corrosion resistance, electrical resistivity and temperature stability. The non-conductive covering 28 can be made of any suitable material, and is preferably made of a biocompatible plastic such as polyurethane or PEBAX.

A series of ring electrodes 36 are mounted on the non-conductive covering 28 of the generally circular main region 39 of the mapping assembly 17. The ring electrodes 36 can be made of any suitable solid conductive material, such as platinum or gold, preferably a combination of platinum and iridium, and mounted onto the non-conductive covering 28 with glue or the like. Alternatively, the ring electrodes can be formed by coating the non-conductive covering 28 with an electrically conducting material, like platinum, gold and/or iridium. The coating can be applied using sputtering, ion beam deposition or an equivalent technique.

In a preferred embodiment, each ring electrode 36 is mounted by first forming a hole in the non-conductive covering 28. An electrode lead wire 50 is fed through the hole, and the ring electrode 36 is welded in place over the lead wire and non-conductive covering 28. The lead wires 50 extend between the non-conductive covering 28 and the support member 24. The proximal end of each lead wire 50 is electrically connected to a suitable connector 37, which is connected to a source of RF energy (not shown).

Figure 7:
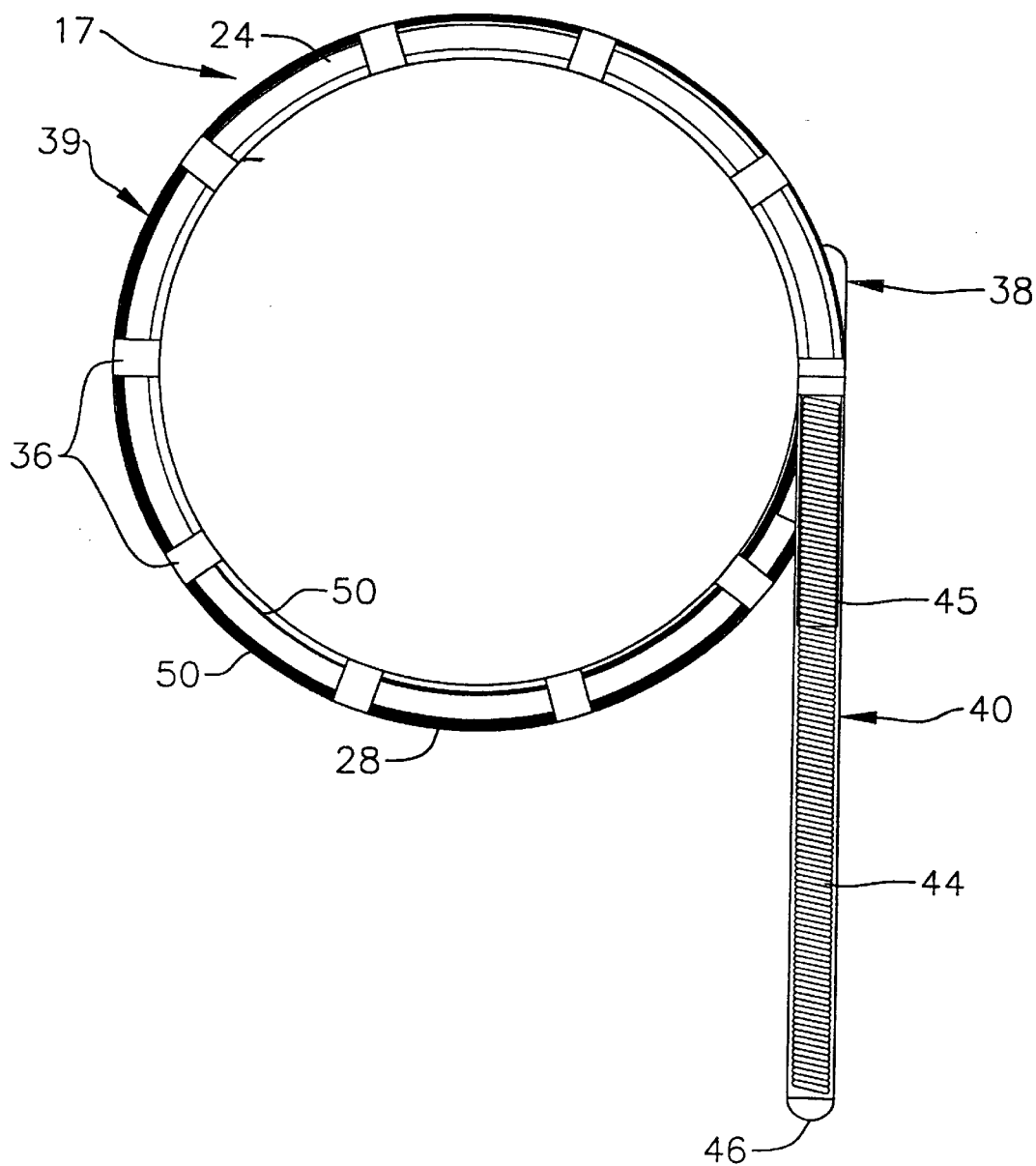
FIG. 7 is a schematic view of the mapping assembly according to the invention.

The number of ring electrodes 36 on the assembly can vary as desired. Preferably the number of ring electrodes ranges from about six to about twenty, preferably from about eight to about twelve. In a particularly preferred embodiment, the assembly carries ten ring electrodes. The ring electrodes 36 are preferably approximately evenly spaced around the generally circular main region 39, as best shown in FIG. 7. In a particularly preferred embodiment, a distance of approximately 5 mm is provided between the centers of the ring electrodes 36.

Figure 8:
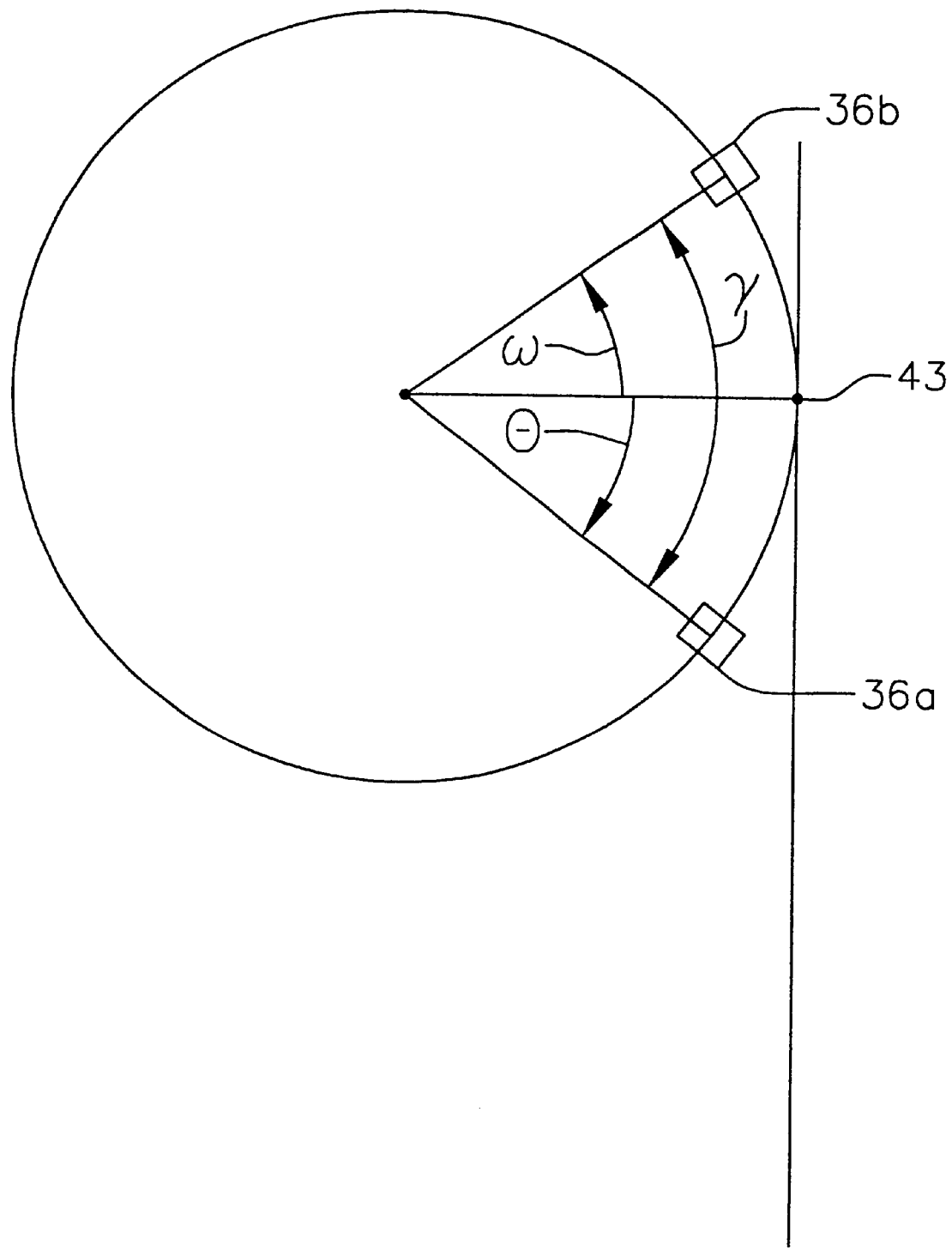
FIG. 8 is a schematic view of the mapping assembly according to the invention depicting the relationship between the first and last electrodes.

FIGS. 7 and 8 show a particularly preferred electrode arrangement. As explained above, the generally circular main region 39 is very slightly helical, although FIGS. 7 and 8 depict the main region as a flat circle, as it would generally appear when viewed from the distal end of the catheter. The generally straight distal region 40 forms a tangent relative to the generally circular main region 39 and contacts the main region at a tangent point 43. A first electrode 36a is provided, which is the electrode that is on the generally circular main region 39 closest to the proximal region 38. A second electrode 36b is provided, which is the electrode that is on the generally circular main region 39 closest to the distal region 40. Preferably, the first electrode 36a is positioned along the circumference of the generally circular main region 39 at a distance θ of no more than about 55° from the tangent point, more preferably no more than about 48° from the tangent point, still more preferably from about 15° to about 36° from the tangent point. Preferably the second electrode 36*b* is positioned along the circumference of the generally circular main region 39 at a distance ω of no more than about 55° degrees from the tangent point, more preferably no more than about 48° from the tangent point, still more preferably from about 15° to about 36° from the tangent point. Preferably the first electrode 36*a* is positioned along the circumference of the generally circular main region 39 at a distance γ of no more than 100° from the second electrode 36*b*, preferably no more than 80° from the second electrode, still more preferably from about 30° to about 75° from the second electrode.

If desired, additional electrodes (not shown) could be mounted along the intermediate section 14, the generally straight proximal section 39, the transition region 41, and generally straight distal region 40.

The generally straight distal region 40 is provided with an atraumatic design to prevent the distal end of the mapping assembly 17 from penetrating tissue. In the depicted embodiment, the distal region 40 comprises a tightly wound coil spring 44 made, for example, of stainless steel, such as the mini guidewire commercially available from Cordis Corporation (Miami, Fla.) or a coil having a 0.0045 inch wire size and a 0.009 inch inner diameter, such as that commercially available from Microspring. The coil spring 44 is mounted at its proximal end in a short piece of tubing 45 with polyurethane glue or the like, which is then glued or otherwise anchored within the non-conductive covering 28. The tubing 45 is less flexible than the non-conductive covering 28 but more flexible than that support member 24 to provide a transition in flexibility along the length of the mapping assembly 17. The distal end of the distal region 40 is capped, preferably with polyurethane glue 46, to prevent body fluids from entering the mapping assembly 17. In the depicted embodiment, the generally straight distal region 40 has a length of about 0.5 inch, but can be any desired length, for example, ranging from about 0.25 inch to about 1.0 inch. The generally straight distal region 40 is preferably sufficiently long to serve as an anchor for introducing the catheter into a guiding sheath, as discussed in more detail below, because the mapping assembly 17 must be straightened upon introduction into the sheath. Without having the generally straight distal region 40 as an anchor, the mapping assembly 17 has a tendency to pull out of the guiding sheath upon its introduction into the guiding sheath. Additionally, if desired, the distal region 40 can be formed, at least in part, of a radiopaque material to aid in the positioning of the mapping assembly 17 under fluoroscopy.

The junction of the intermediate section 14 and mapping assembly 17 is shown in FIG. 3. The non-conductive covering 28 is attached to the tubing 22 of the intermediate section by glue or the like. The support member 24 extends from the third lumen 32 into the non-conductive covering 28. The proximal end of the support member 24 terminates a short distance within the third lumen 32, approximately about 5 mm, so as not to adversely affect the ability of the intermediate section 14 to deflect. However, if desired, the proximal end of the support member 24 can extend into the catheter body 12.

The lead wires 50 attached to the ring electrodes 36 extend through the first lumen 30 of the intermediate section 14, through the central lumen 18 of the catheter body 12, and the control handle 16, and terminate at their proximal end in the connector 37. The portion of the lead wires 50 extending through the central lumen 18 of the catheter body 12, control handle 16 and proximal end of the intermediate section 14 are enclosed within a protective sheath 62, which can be made of any suitable material, preferably polyimide. The protective sheath 62 is anchored at its distal end to the proximal end of the intermediate section 14 by gluing it in the first lumen 30 with polyurethane glue or the like.

The puller wire 64 is provided for deflection of the intermediate section 14. The puller wire 64 extends through the catheter body 12, is anchored at its proximal end to the control handle 16, and is anchored at its distal end to the intermediate section 14. The puller wire 64 is made of any suitable metal, such as stainless steel or Nitinol, and is preferably coated with Teflon® or the like. The coating imparts lubricity to the puller wire 64. The puller wire 64 preferably has a diameter ranging from about 0.006 to about 0.010 inch.

A compression coil 66 is situated within the catheter body 12 in surrounding relation to the puller wire 64. The compression coil 66 extends from the proximal end of the catheter body 12 to the proximal end of the intermediate section 14. The compression coil 66 is made of any suitable metal, preferably stainless steel. The compression coil 66 is tightly wound on itself to provide flexibility, i.e., bending, but to resist compression. The inner diameter of the compression coil 66 is preferably slightly larger than the diameter of the puller wire 64. The Teflon® coating on the puller wire 64 allows it to slide freely within the compression coil 66. The outer surface of the compression coil 66 is covered by a flexible, non-conductive sheath 68, e.g., made of polyimide tubing.

The compression coil 66 is anchored at its proximal end to the outer wall 20 of the catheter body 12 by proximal glue joint 70 and at its distal end to the intermediate section 14 by distal glue joint 72. Both glue joints 70 and 72 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surface of the compression coil 66 and wicks around the outer circumference to form a glue joint about the entire circumference of the compression coil.

The puller wire 64 extends into the second lumen 32 of the intermediate section 14. Preferably the puller wire 64 is anchored at its distal end to the distal end of the intermediate section 14, as shown in FIG. 3. Specifically, a T-shaped anchor is formed, which comprises a short piece of tubular stainless steel 80, e.g., hypodermic stock, which is fitted over the distal end of the puller wire 64 and crimped to fixedly secure it to the puller wire. The distal end of the tubular stainless steel 80 is fixedly attached, e.g., by welding, to a cross-piece 82 formed of stainless steel ribbon or the like. The cross-piece 82 sits beyond the distal end of the second lumen 32. The cross-piece 82 is larger than the lumen opening and, therefore, cannot be pulled through the opening. The distal end of the second lumen 32 is then filled with glue or the like, preferably a polyurethane glue. Within the second lumen 32 of the intermediate section 14, the puller wire 64 extends through a plastic, preferably Teflon®, puller wire sheath (not shown), which prevents the puller wire 64 from cutting into the wall of the intermediate section 14 when the intermediate section is deflected.

Longitudinal movement of the puller wire 42 relative to the catheter body 12, which results in deflection of the intermediate section 14, is accomplished by suitable manipulation of the control handle 16. Examples of suitable control handles for use in the present invention are disclosed, for example, in U.S. Pat. Nos. Re 34,502 and 5,897,529, the entire disclosures of which are incorporated herein by reference.

In use, a suitable guiding sheath is inserted into the patient with its distal end positioned at a desired mapping location. An example of a suitable guiding sheath for use in connection with the present invention is the Preface™ Braiding Guiding Sheath, commercially available from Cordis Webster (Diamond Bar, Calif.). The distal end of the sheath is guided into one of the atria. A catheter in accordance with the present invention is fed through the guiding sheath until its distal end extends out of the distal end of the guiding sheath. As the catheter is fed through the guiding sheath, the mapping assembly 17 is straightened to fit through the sheath. Once the distal end of the catheter is positioned at the desired mapping location, the guiding sheath is pulled proximally, allowing the deflectable intermediate section 14 and mapping assembly 17 to extend outside the sheath, and the mapping assembly 17 returns to its original shape due to the shape-memory of the support member 24. The mapping assembly 17 is then inserted into a pulmonary vein or other tubular region (such as the coronary sinus, superior vena cava, or inferior vena cava) so that the outer circumference of the generally circular main region 39 of the assembly is in contact with a circumference inside the tubular region. Preferably at least about 50%, more preferably at least about 70%, and still more preferably at least about 80% of the circumference of the generally circular main region is in contact with a circumference inside the tubular region.

The circular arrangement of the electrodes 36 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or the coronary sinus. Additionally, because the main region 39 preferably does not form a flat circle, but instead is somewhat helical, as shown in FIG. 4, it is easier for the user to guide the mapping assembly 17 into a tubular region.

If desired, two or more puller wires can be provided to enhance the ability to manipulate the intermediate section. In such an embodiment, a second puller wire and a surrounding second compression coil extend through the catheter body and into an additional off-axis lumen in the intermediate section. The first puller wire is preferably anchored proximal to the anchor location of the second puller wire. Suitable designs of catheters having two or more puller wires, including suitable control handles for such embodiments, are described, for example, in U.S. patent application Ser. No. 08/924,611, filed Sep. 5, 1997; Ser. No. 09/130,359; , filed Aug. 7, 1998; Ser. No. 09/143,426, filed Aug. 28, 1998; and Ser. No. 09/157,055, filed Sep. 18, 1998, the disclosures of which are incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A method for mapping electrical activity within a tubular region of or near the heart having a inner circumference, the method comprising:
   inserting into the heart the distal end of a catheter comprising:
      an elongated tubular catheter body having an outer wall, proximal and distal ends, and at least one lumen extending therethrough; and
      a mapping assembly comprising:
         a tubular structure having a generally straight proximal region attached to the catheter body, a generally circular main region generally transverse and distal to the proximal region having an outer circumference, a transition region connecting the proximal region and the main region, and a generally straight distal region distal the main region, wherein the tubular structure comprises a nonconductive cover over at least the main region of the mapping assembly, and
         a plurality of spaced-apart electrodes carried by the generally circular main region of the mapping assembly;
   contacting the outer circumference of the generally circular main region with the inner circumference of the tubular region; and
   mapping the electrical activity within the tubular region with the electrodes along the generally circular main region.

2. A method according to claim 1, further comprising an intermediate section between the catheter body and the mapping assembly, the intermediate section having at least one lumen extending therethrough and being more flexible than the catheter body.

3. A method according to claim 2, wherein the intermediate section has three lumens extending therethrough.

4. A method according to claim 1, wherein the transition region is slightly curved and formed such that, when viewed from the side of the catheter with the proximal region at the top of the circular main region, the proximal region forms an angle α with the circular region ranging from about 75° to about 95°.

5. A method according to claim 1, wherein the transition region is slightly curved and formed such that, when viewed from the side of the catheter with the proximal region at the top of the circular main region, the proximal region forms an angle α with the circular main region ranging from about 83° to about 93°.

6. A method according to claim 1, wherein the number of electrodes along the generally circular main region ranges from about six to about twenty.

7. A method according to claim 1, wherein the number of electrodes along the generally circular main region ranges about eight to about twelve.

8. A method according to claim 6, wherein the electrodes are approximately evenly spaced around the generally circular main region.

9. A method according to claim 1, wherein the generally straight proximal region has an exposed length ranging from about 3 mm to about 12 mm.

10. A method according to claim 1, wherein the generally straight proximal region has an exposed length ranging from about 3 mm to about 8 mm.

11. A method according to claim 1, wherein the generally straight proximal region extends substantially tangentially to the generally circular main region.

12. A method according to claim 1, wherein the generally straight distal region has an atraumatic design to prevent the distal end of the mapping assembly from penetrating tissue.

13. A method according to claim 1, wherein the generally straight distal region comprises a tightly wound coil spring.

14. A method according to claim 13, wherein the coil spring is contained within the non-conductive covering.

15. A method according to claim 1, wherein the generally straight distal region has a length ranging from about 0.25 inch to about 1.0 inch.

16. A method according to claim 2, further comprising a control handle mounted at the proximal end of the catheter body and means for deflecting the intermediate section by manipulation of the control handle.

17. A method according to claim 16, wherein the control handle comprises a first member fixedly attached to the proximal end of the catheter body and a second member that is movable relative to the first member.

18. A method according to claim 17, wherein the deflecting means comprises a puller wire having a proximal end and a distal end, the puller wire extending from the control handle, through the catheter body and into the a lumen in the intermediate section, wherein the distal end of the puller wire is fixedly secured within the intermediate section and the proximal end of the puller wire is fixedly secured to the second member of the control handle, whereby manipulation of the first member of the control handle relative to the second member of the control handle moves the puller wire relative to the catheter body, resulting in deflection of the intermediate section.

19. A method according to claim 1, wherein the tubular region is selected from the group consisting of pulmonary veins, the coronary sinus, the superior vena cava, and the inferior vena cava.

20. A method according to claim 19, wherein the tubular region is a pulmonary vein.

21. A method according to claim 1, wherein the generally circular main region has an outer diameter ranging from about 10 mm to about 25 mm.

22. A method according to claim 1, wherein the generally circular main region has an outer diameter ranging from about 12 mm to about 20 mm.

23. A method according to claim 1, wherein the generally circular main region has an outer diameter of about 15 mm.

24. A method according to claim 1, wherein at least about 50% of the outer circumference of the generally circular main region is in contact with the inner circumference of the tubular region.

25. A method according to claim 1, wherein at least about 70% of the outer circumference of the generally circular main region is in contact with the inner circumference of the tubular region.

26. A method according to claim 1, wherein at least about 80% of the outer circumference of the generally circular main region is in contact with the inner circumference of the tubular region.

27. A method according to claim 1, wherein the mapping assembly comprises a plurality of electrodes carried by the generally circular main region of the mapping assembly, wherein the electrodes are generally evenly spaced about the entire circumference of the mapping assembly such that, in use, when the mapping assembly is positioned in a tubular region of or near the heart, with the outer circumference of the generally circular main region in contact with the inner circumference of the tubular region, the electrodes can be used to map the inner circumference of the tubular region.

28. A method according to claim 27, wherein the circular main region has first and second ends, and further wherein a first electrode is positioned on the generally circular main region a distance of no more than about 55° from the first end, a second electrode is positioned on the generally circular main region a distance of no more than about 55° from the second end, and a plurality of additional electrodes are approximately evenly spaced along the length of the generally circular main region between the first electrode and the second electrode.

29. A method according to claim 28, wherein the first electrode is positioned on the generally circular main region a distance of no more than about 48° from the first end, and the second electrode is positioned on the generally circular main region a distance of no more than about 48° from the second end.

30. A method according to claim 28, wherein the first electrode is positioned on the generally circular main region a distance ranging from about 15° to about 36° from the first end, and the second electrode is positioned on the generally circular main region a distance ranging from about 15° to about 36° from the second end.

31. A method according to claim 1, wherein the mapping assembly further comprises a support member having shape-memory disposed within at least the main region of the mapping assembly.

32. A method for mapping electrical activity within a tubular region of or near the heart having a inner circumference, the method comprising:
inserting into the heart the distal end of a catheter comprising:
an elongated flexible tubular catheter body having an axis and proximal and distal ends;
a mapping assembly at the distal end of the tubular body comprising a compound curve having a first bend away from the axis of the catheter body and a second bend having a preformed generally circular curve transverse to the axis of the catheter body, said mapping assembly having proximal and distal ends and carrying a plurality of spaced apart electrodes;
an electrode lead wire associated with each electrode, each electrode lead wire having proximal and distal ends and extending through the catheter body and into the mapping assembly, the distal end of each electrode lead wire being electrically connected to its associated electrode;
a puller wire having proximal and distal ends extending through the tubular catheter body, the distal end of the puller wire being fixedly attached to the distal end of the catheter body; and
a handle connected to the proximal ends of the catheter body and puller wire for moving the puller wire longitudinally relative to the catheter body, whereby longitudinal movement of the puller wire relative to the catheter body results in deflection of the distal end of the catheter body;
contacting the outer circumference of the preformed generally circular curve with the inner circumference of the tubular region; and
mapping the electrical activity within the tubular region with the electrodes along the mapping assembly.

33. A method according to claim 32, wherein the compound curve has an outer diameter ranging from about 10 mm to about 25 mm.

34. A method according to claim 32, wherein the compound curve has an outer diameter ranging from about 12 mm to about 20 mm.

35. A method according to claim 32, wherein the number of electrodes on the mapping assembly ranges from about eight to about twelve.

36. A method according to claim 32, wherein the mapping assembly further comprises a distal region distal to the compound curve, the distal region being more flexible than the compound curve.

37. A method according to claim 32, wherein the mapping assembly further comprises a generally straight distal region distal to the compound curve.

38. A method according to claim 37, wherein the generally straight distal region is more flexible than the compound curve.

39. A method for mapping electrical activity within a tubular region of or near the heart having a inner circumference, the method comprising:
   inserting into the heart a distal end of a catheter comprising:
      an elongated tubular catheter body having an outer wall, proximal and distal ends, and at least one lumen extending therethrough; and
      a mapping assembly comprising a tubular structure having a generally circular main region generally transverse and distal to the catheter body and having an outer circumference and an outer diameter ranging from about 10 mm to about 25 mm, wherein the tubular structure has at least one electrode carried by the generally circular main region of the mapping assembly;
   contacting the outer circumference of the generally circular main region with the inner circumference of the tubular region; and
   mapping the electrical activity within the tubular region with the at least one electrode along the generally circular main region.

40. A method according to claim 39, wherein the tubular structure comprises a non-conductive cover over at least the main region of the mapping assembly and a support member having shape-memory disposed within at least the main region of the mapping assembly.

41. A method according to claim 39, wherein the mapping assembly further comprises a generally straight distal region distal to the main region.

42. A method according to claim 39, wherein the distal region is more flexible than the main region.

43. A method according to claim 39, wherein the mapping assembly further comprises a distal region distal to the main region, wherein the distal region is more flexible than the main region.

44. A method according to claim 39, wherein the mapping assembly comprises a plurality of electrodes carried by the generally circular main region of the mapping assembly, wherein the electrodes are generally evenly spaced about the entire circumference of the mapping assembly such that, in use, when the mapping assembly is positioned in a tubular region of or near the heart, with the outer circumference of the generally circular main region in contact with the inner circumference of the tubular region, the electrodes can be used to map the inner circumference of the tubular region.

45. A method according to claim 44, wherein the circular main region has first and second ends, and further wherein a first electrode is positioned on the generally circular main region a distance of no more than about 55° from the first end, a second electrode is positioned on the generally circular main region a distance of no more than about 55° from the second end, and a plurality of additional electrodes are approximately evenly spaced along the length of the generally circular main region between the first electrode and the second electrode.

46. A method according to claim 45, wherein the first electrode is positioned on the generally circular main region a distance of no more than about 48° from the first end, and the second electrode is positioned on the generally circular main region a distance of no more than about 48° from the second end.

47. A method according to claim 45, wherein the first electrode is positioned on the generally circular main region a distance ranging from about 15° to about 36° from the first end, and the second electrode is positioned on the generally circular main region a distance ranging from about 15° to about 36° from the second end.

48. A method according to claim 39, wherein the generally circular main region has an outer diameter ranging from about 12 mm to about 20 mm.

49. A catheter according to claim 39, wherein the number of electrodes along the generally circular main region ranges from about six to about twenty.

50. A method according to claim 39, wherein the number of electrodes along the generally circular main region ranges about eight to about twelve.

51. A method according to claim 39, further comprising means for deflecting the distal end of the catheter body without altering the shape of the mapping assembly.

52. A method according to claim 51, wherein the deflecting means comprises:
   a puller wire extending through a lumen of the catheter body, said puller wire being fixedly attached at its distal end to the catheter body near the catheter body's distal end; and
   a control handle for moving the puller wire longitudinally relative to the catheter body to thereby cause deflection of the distal end of the catheter body.

53. A method according to claim 39, wherein the tubular region is selected from the group consisting of pulmonary veins, the coronary sinus, the superior vena cava, and the inferior vena cava.

54. A method according to claim 39, wherein the tubular region is a pulmonary vein.

55. A method according to claim 39, wherein at least about 50% of the outer circumference of the generally circular main region is in contact with the inner circumference of the tubular region.

56. A method according to claim 39, wherein at least about 70% of the outer circumference of the generally circular main region is in contact with the inner circumference of the tubular region.

57. A method according to claim 39, wherein at least about 80% of the outer circumference of the generally circular main region is in contact with the inner circumference of the tubular region.

58. A method according to claims 39, wherein the generally circular main region consists of a single generally circular curve.

59. A method according to claim 39, wherein, when the catheter is viewed from the side with the catheter body positioned at the top of the generally circular main region, the catheter body forms an angle with the generally circular main region ranging from about 75° to about 95°.

60. A catheter according to claim 39, wherein, when the catheter is viewed from the side with the catheter body positioned at the top of the generally circular main region, the catheter body forms an angle with the generally circular main region ranging from about 83° to about 93°.

61. A method according to claim 51, wherein the deflecting means comprises:
   a puller wire extending through a lumen of the catheter body, said puller wire being fixedly attached at its distal end to the catheter body near the catheter body's distal end; and a control handle for moving the puller wire longitudinally relative to the catheter body to thereby cause deflection of the distal end of the catheter body.

62. A method for mapping electrical activity within a tubular region of or near the heart having a inner circumference, the method comprising:

inserting into the heart a distal end of a catheter comprising:

an elongated tubular catheter body having an outer wall, proximal and distal ends, and at least one lumen extending therethrough; and a mapping assembly at the distal end of the catheter body, the mapping assembly comprising a plurality of electrodes arranged about a circumference of the mapping assembly;

contacting the circumference of the mapping assembly with the inner circumference of the tubular region, wherein at least about 50% of the circumference of the mapping assembly is in contact with the inner circumference of the tubular region; and mapping the electrical activity within the tubular region with the plurality of electrodes.

63. A method according to claim 62, wherein the mapping assembly comprises a non-conductive cover over at least a portion of the mapping assembly and a support member having shape-memory disposed within at least a portion of the mapping assembly.

64. A method according to claim 62, wherein the number of electrodes along the mapping assembly ranges from about eight to about twelve.

65. A method according to claim 62, further comprising means for deflecting the distal end of the catheter body without altering the shape of the mapping assembly.

66. A method according to claim 65, wherein the deflecting means comprises:

a puller wire extending through a lumen of the catheter body, said puller wire being fixedly attached at its distal end to the catheter body near the catheter body's distal end; and a control handle for moving the puller wire longitudinally relative to the catheter body to thereby cause deflection of the distal end of the catheter body.

67. A method according to claim 62, wherein the tubular region is selected from the group consisting of pulmonary veins, the coronary sinus, the superior vena cava, and the inferior vena cava.

68. A method according to claim 62, wherein the tubular region is a pulmonary vein.

69. A method according to claim 62, wherein at least about 80% of the circumference of the mapping assembly is in contact with the inner circumference of the tubular region.

70. A method for mapping electrical activity within a tubular region of or near the heart having a inner circumference, the method comprising:

inserting into the heart a distal end of a catheter comprising:

an elongated tubular catheter body having an outer wall, proximal and distal ends, and at least one lumen extending therethrough; and a mapping assembly comprising a tubular structure having a generally circular main region generally transverse and distal to the catheter body and having an outer circumference, wherein the tubular structure has at least one electrode carried by the generally circular main region of the mapping assembly;

contacting the outer circumference of the generally circular main region with the inner circumference of the tubular region, wherein at least about 50% of the outer circumference of the generally circular main region is in contact with the inner circumference of the tubular region; and mapping the electrical activity within the tubular region with the at least one electrode along the generally circular main region.

71. A method according to claim 70, wherein the tubular structure comprises a non-conductive cover over at least the main region of the mapping assembly and a support member having shape-memory disposed within at least the main region of the mapping assembly.

72. A method according to claim 70, wherein the mapping assembly comprises a plurality of electrodes carried by the generally circular main region of the mapping assembly, wherein the electrodes are generally evenly spaced about the entire circumference of the mapping assembly.

73. A method according to claim 70, wherein the generally circular main region has an outer diameter ranging from about 12 mm to about 20 mm.

74. A catheter according to claim 70, wherein the number of electrodes along the generally circular main region ranges from about six to about twenty.

75. A method according to claim 70, wherein the number of electrodes along the generally circular main region ranges about eight to about twelve.

76. A method according to claim 70, further comprising means for deflecting the distal end of the catheter body without altering the shape of the mapping assembly.

77. A method according to claim 70, wherein the deflecting means comprises:

a puller wire extending through a lumen of the catheter body, said puller wire being fixedly attached at its distal end to the catheter body near the catheter body's distal end; and a control handle for moving the puller wire longitudinally relative to the catheter body to thereby cause deflection of the distal end of the catheter body.

78. A method according to claim 70, wherein the tubular region is selected from the group consisting of pulmonary veins, the coronary sinus, the superior vena cava, and the inferior vena cava.

79. A method according to claim 70, wherein the tubular region is a pulmonary vein.

80. A method according to claim 70, wherein at least about 70% of the outer circumference of the generally circular main region is in contact with the inner circumference of the tubular region.

81. A method according to claim 70, wherein at least about 80% of the outer circumference of the generally circular main region is in contact with the inner circumference of the tubular region.

82. A method according to claim 70, wherein the generally circular main region consists of a single generally circular curve.

* * * * *